(12) United States Patent
Egídio Rodrigues et al.

(10) Patent No.: US 7,488,851 B2
(45) Date of Patent: Feb. 10, 2009

(54) INDUSTRIAL PROCESS FOR ACETALS PRODUCTION IN A SIMULATED MOVING BED REACTOR

(75) Inventors: Alírio Egídio Rodrigues, Porto (PT); Viviana Manuela Tenedório Matos Da Silva, Porto (PT)

(73) Assignee: Universidade Do Porto, Porto (PT)

( * ) Notice: Subject to any disclaimer, the term of this patent is extended or adjusted under 35 U.S.C. 154(b) by 13 days.

(21) Appl. No.: 11/596,213

(22) PCT Filed: May 17, 2005

(86) PCT No.: PCT/IB2005/051597

§ 371 (c)(1),
(2), (4) Date: Aug. 14, 2007

(87) PCT Pub. No.: WO2005/113476

PCT Pub. Date: Dec. 1, 2005

(65) Prior Publication Data

US 2008/0287714 A1    Nov. 20, 2008

(30) Foreign Application Priority Data

May 19, 2004    (PT) ..................... 103123

(51) Int. Cl.
C07C 41/56    (2006.01)
C07C 43/30    (2006.01)

(52) U.S. Cl. .................. 568/594; 568/596; 568/605

(58) Field of Classification Search ............... 568/594, 568/596, 605
See application file for complete search history.

(56) References Cited

U.S. PATENT DOCUMENTS

| | | | | |
|---|---|---|---|---|
| 2,519,540 A | * | 8/1950 | Bramwyche et al. | 568/605 |
| 4,579,979 A | * | 4/1986 | Andrade et al. | 568/596 |
| 5,362,918 A | * | 11/1994 | Aizawa et al. | 568/594 |
| 5,405,992 A | | 4/1995 | Funk et al. | |
| 5,527,969 A | * | 6/1996 | Kaufhold et al. | 568/605 |
| 6,476,239 B1 | * | 11/2002 | Arumugam et al. | 549/315 |
| 6,518,454 B1 | * | 2/2003 | Arumugam et al. | 560/265 |

OTHER PUBLICATIONS

M. F. Gomex, Ma C. Abello:, "Synthesis of 1, 1-Diethoxyethane Using a Continuous Flow Reactor: Catalyst Deactivation and Effect of Feed Purity and of Solvent Addition", J. Chem. Tech. Biotech., 'Online!, vol. 79, No. 4, 2004, pp. 391-396, XP002352997, Retrieved From the Internet: URL:http://www3.interscience.wiley.com/cgibin/fulltext/107637609/PDFSTART>, 'Retrieved on Nov. 8, 2005.

Alirio E. Rodrigues, Viviana M. T. M. Sliva:, "Synthesis of Diethylacetal: Thermodynamic and Kinetic Studies", Chem. Eng. Science, 'Online!, vol. 56, 2001, pp. 1255-1263, XP002352998, Retrieved from the Internet: URL:http://www.sciencedirect.com/science?_ob=MImg&_imagekey=B6TFK—42HFNY7-6-8K&_cdi=5229&_user=987766&_orig=browse&_coverDate—02%2F28%2F2001&_sk=999439995&view=c&wchp=dGLbVtb-zSkWA&md5=b7f6984836fae9b117613e7e57130ad3&ie-/sdarticle.pdf>, 'Retrieved on Nov. 8, 2005!.

F. Lode, M. Mazzoti, M. Morbidelli:, "A New Reaction-Separation Unit: The Simulated Moving Bead Reactor", Chimia, 'Online!, vol. 55, No. 10, 2001, pp. 883-886, XPOO2352999, Retrieved from the Internet:, URL:http://www.chab.ethz.ch/publicrelations/publikationen/chimia/f19.pdf>, 'Retrieved on Nov. 8, 2005!.

* cited by examiner

Primary Examiner—Sikarl A Witherspoon
(74) Attorney, Agent, or Firm—Sughrue Mion, PLLC

(57) ABSTRACT

The present invention is an industrial process for the preparation of acetals using a simulated moving bed (SMB) reactor system to accomplish the conversion of reactants (aldehyde and alcohol) and simultaneously, the separation of the reaction products (acetal and water) by selective adsorption. The SMB reactor consists of a set of interconnected columns packed with an acid solid (or mixture of acid solids: catalysts and adsorbents) effective for catalyzing the reaction between aldehydes and alcohols and for separating the reaction products by selective adsorption of at least one product. In a general embodiment, this process involves (1) feeding a mixture of aldehydes and alcohols and a desorbent which is the alcohol, to a simulated moving bed reactor; (2) reacting aldehydes and alcohols to form acetals; and (3) removing from the simulated moving bed reactor two liquid streams, a first liquid stream comprising a solution of acetal in the desorbent (raffinate), a second liquid stream comprising the water formed and the desorbent (extract).

18 Claims, 2 Drawing Sheets

Figure 2.
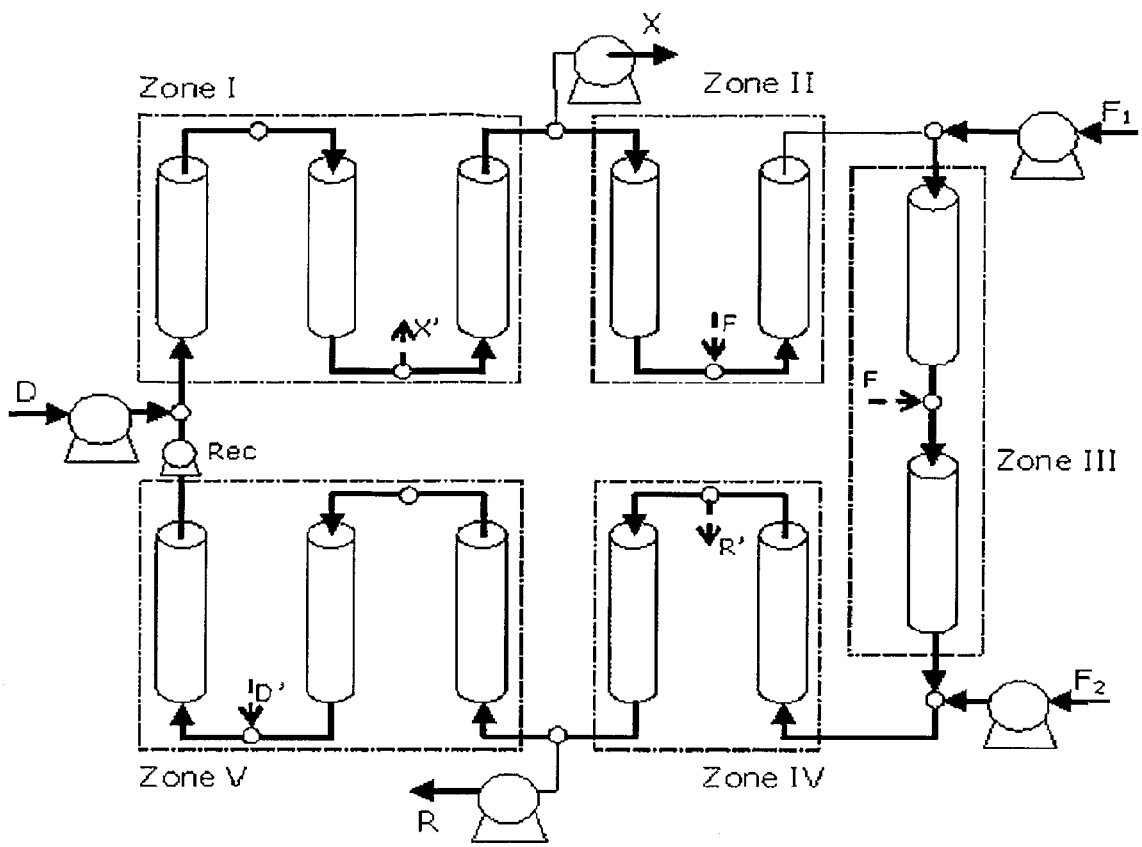
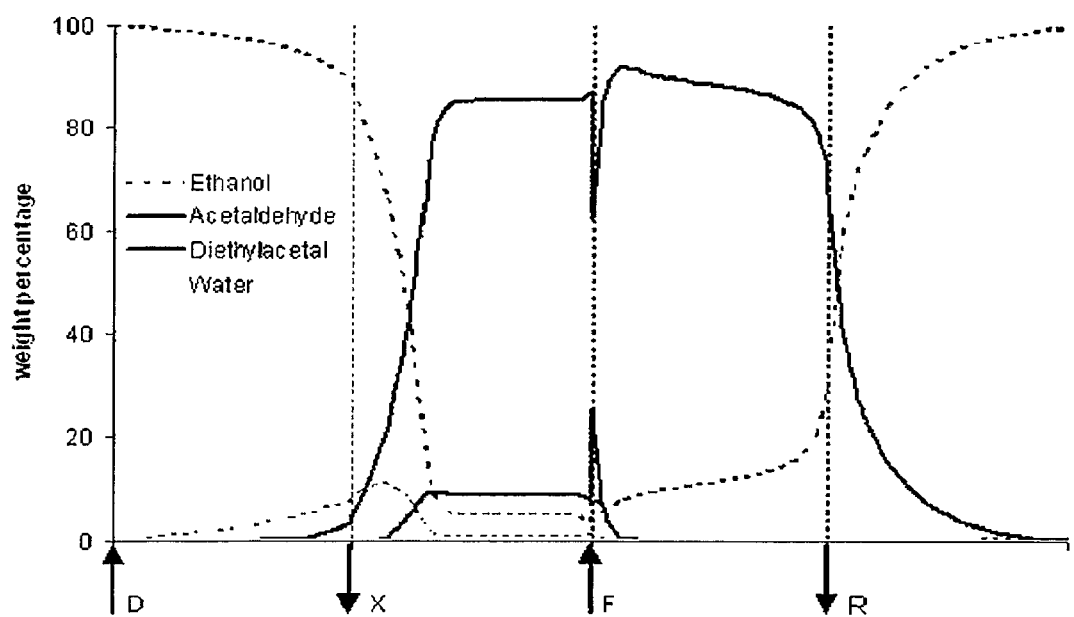
Figure 3.

INDUSTRIAL PROCESS FOR ACETALS PRODUCTION IN A SIMULATED MOVING BED REACTOR

FIELD OF THE INVENTION

This invention relates to a novel process for the continuous preparation of acetals at industrial scale in a simulated moving bed reactor (SMBR).

BACKGROUND OF THE INVENTION

The acetals with chemical structure $R_2$—CH—(O—$R_1$)$_2$ are oxygenated compounds produced by the reaction between an aldehyde ($R_2$—CHO) and an alcohol ($R_1$—OH) in the presence of an acid catalyst, accordingly to:

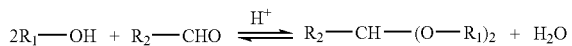

$$2R_1\text{—OH} + R_2\text{—CHO} \xrightleftharpoons{H^+} R_2\text{—CH—(O—}R_1)_2 + H_2O$$

Traditionally, the reaction is catalyzed by mineral or carboxylic acids (U.S. Pat. No. 2,519,540, U.S. Pat. No. 5,362,918 and U.S. Pat. No. 5,527,969). The disadvantage of using soluble catalyst is that they must be neutralized after reaction and separated from the product. Therefore, heterogeneous catalysts as ion exchange resins (acid type) or zeolites are used, which have the advantage of being easily separated from reaction product and having a long lifetime (patents EP 1 167 333 A2 and U.S. Pat. No. 4,579,979).

The synthesis of acetals is a reversible reaction. In order to obtain acceptable acetal yields, the equilibrium must be displaced in the direction of acetal synthesis. Several methods are used to displace equilibrium towards acetal formation, such as:
1. to use a large excess of one of the reactants, in general the alcohol, which then requires elimination of that excess in a step of purification of the desired product (U.S. Pat. No. 5,362,918);
2. to use an organic solvent to eliminate water by azeotropic distillation between a solvent and water or by liquid-liquid extraction, a further step of separation is necessary to remove the solvent from the end product (U.S. Pat. No. 2,519,540, U.S. Pat. No. 4,579,979, U.S. Pat. No. 5,362,918 e U.S. Pat. No. 5,527,969);
3. to use reactive separations in order to remove the products from the reaction medium, being the reactive distillation process the most common (U.S. Pat. No. 5,362,918).

The processes described above introduce some improvement in the acetals production; however, they also have several disadvantages. For the first method, the conversion of the limiting reactant increases but the yield of the reaction decreases. The second one presents higher conversions but it is necessary to use a solvent; consequently, the costs of raw materials and equipment increase. The reactive distillation could not be applied to all systems, due to azeotropes formation and/or to the incompatible volatilities of reactants and products. It is also possible by-products formation.

In recent times, in addition to the well-known acetals applications, they have been considered as diesel oil additives, mainly acetaldehyde diethylacetal. It is confirmed that the use of acetals decreases the emissions of particles and $NO_x$ while keeping or improving the cetane number and helping in the combustion of the final products, without decreasing the ignition quality (patents DE 2 911 411, DE 3 136 030, WO 2001/181 154 A1, WO 2002/026 744 A1).

BRIEF DESCRIPTION OF THE FIGURES

FIG. 2 shows a second schematic representation of the SMBR process of the present invention, where the reactants (alcohol and aldehyde) are introduced separately in different feed streams.

FIG. 3 shows the internal concentration profiles in a SMBR at the middle of a switching time at cyclic steady-state.

SUMMARY OF THE INVENTION

Figure 1:
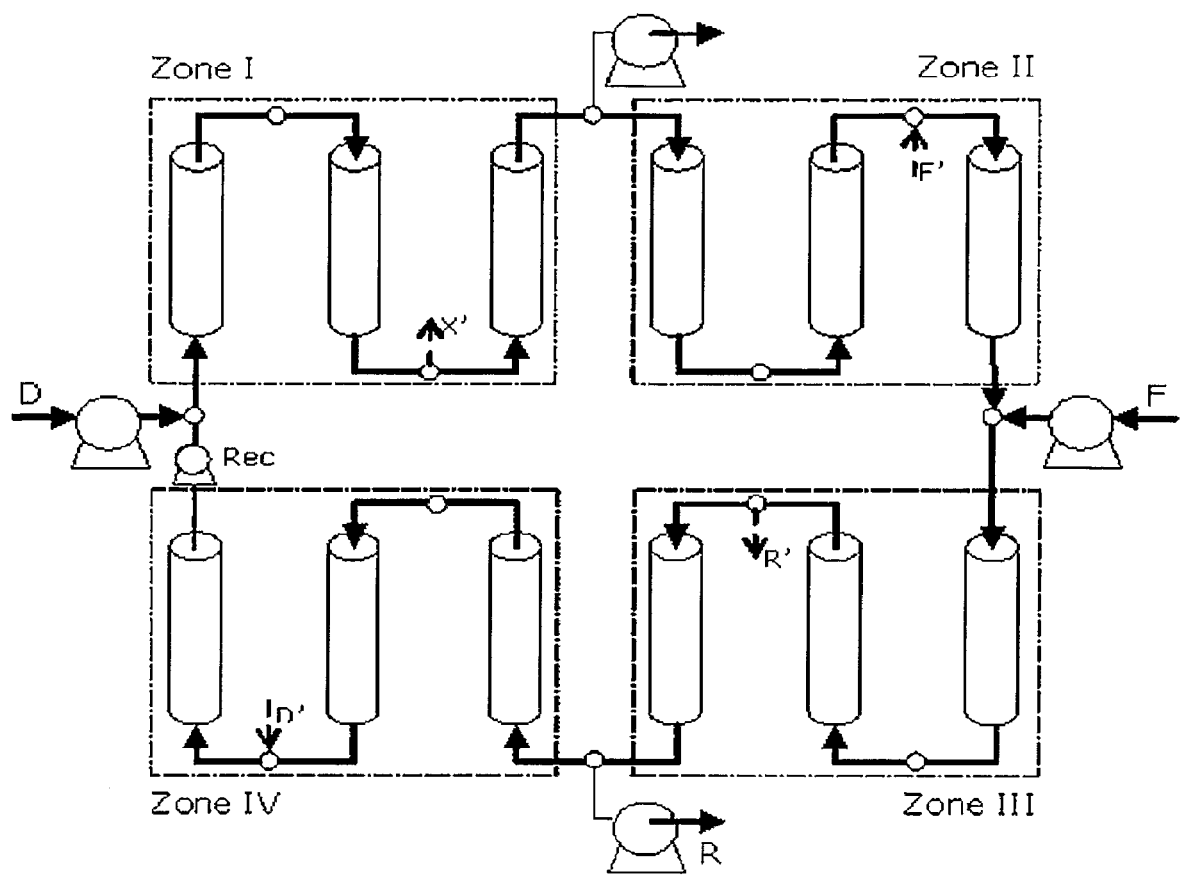
FIG. 1 shows a schematic representation of the SMBR process of the present invention, where both reactants (alcohol and aldehyde) are introduced in a single feed stream.

The purpose of the invention is to provide an alternative process for acetals manufacture, achieving 100% of aldehyde conversion, without using additional organic solvents and without by-products formation.

The acetals produced by the process of the present invention are used in the formulation of perfumes and in the flavouring of alcoholic beverages. Acetal also finds widespread use as intermediate for the synthesis of various industrial chemicals used for agriculture and pharmaceuticals (vitamins and analgesics). Particularly, acetaldehyde diethylacetal is used as solvent and intermediate in the process where the protection of carboxylic groups of aldehydes is needed. Diethylacetal is also used as diesel oil additive, since decreases the emissions of particles and $NO_x$.

DETAILED DESCRIPTION OF THE INVENTION

The present invention is concerned with an efficient and continuous process for the preparation of acetals which comprises simultaneously reaction of a lower aliphatic aldehyde with a lower aliphatic alcohol in the presence of acid solid and separation of the produced acetals from the water formed in the SMBR unit.

The acid solids, that should be simultaneously catalysts and selective adsorbents, could be acidic ion exchange resins, zeolites (Y, mordenites, ZSM, ferrierites), alumina silicates (mortmorillonites and bentonites) or hydrotalcites. Examples of acid resins are Dowex 50 (Dow Chemical), Amberlite IR 120, Amberlyst A15 and A36 (Rohm & Haas), Lewatit (Bayer). These acid solids adsorb preferentially water rather than acetals. Alternatively, it is possible to use a mixture of acid solids as catalyst and as selective adsorbent.

The Simulated Moving Bed Reactor technology is being recently applied for the preparation of esters from carboxylic acids, see, e.g., U.S. Pat. No. 6,518,454 and U.S. Pat. No. 6,476,239. In Simulated Moving Bed based process, the different affinity to the solid adsorbent is used to separate the products.

More precisely, the present invention deals with the process of acetals preparation in a Simulated Moving Bed Reactor, which comprise the reaction between the alcohol and the aldehyde in the presence of an acid solid (or a mixture of a acid solid catalyst and a selective adsorbent) and the simultaneous separation of the reaction products (acetal and water) by adsorption.

Preferentially, this process comprises the following steps:
I. to feed a reactant mixture (alcohol and aldehyde) and a desorbent (alcohol) to the SMBR unit, equipped with a series of columns packed with acid solid (or a mixture of acid solids);
II. to react the alcohol with the aldehyde to produce acetal and water;

III. to remove two streams, a first liquid stream comprising a solution of acetal in the desorbent (raffinate); a second liquid stream comprising the water formed and the desorbent (extract).

The reactor is equipped with a number of inlet and outlet ports, and a number of valves arranged in manner such that any feed stream may be introduced to any column and any outlet or effluent stream may be withdraw from any column. During the operation of the SMB unit, the columns to which the feed streams are fed and from which the outlet streams are withdrawn are periodically moved. To achieve separation of reaction products, the locations of the inlet and outlet streams are moved intermittently in the direction of the liquid flow. The intermittently port movement in the direction of the liquid flow simulates the counter-current of the bed or beds of the solid(s), e.g., the solid catalyst.

The simulated moving bed reactor utilized in the present invention is a known apparatus and comprises several columns per zone; each column is package with a solid or a mixture of solids. As depicted in FIG. 1 and FIG. 2, The SMB reactor typically has 4 or 5 zones.

The lower alcohol has the following chemical structure

where $R_1$ represents an alkyl group $C_1$-$C_8$, linear or branched.

Preferably, the alcohol includes a group such as methyl, ethyl, propyl and butyl. Examples of those alcohols are methanol, ethanol, propanol and butanol.

The lower aldehyde has the following chemical structure

where $R_2$ represents an alkyl group $C_1$-$C_8$, linear or branched.

Preferably, the aldehyde includes a group such as methyl, ethyl, propyl and butyl. Examples of those aldehyde s are formaldehyde, acetaldehyde, propionaldehyde and butyraldehyde.

Therefore, the produced acetal has the following chemical structure

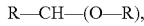

where $R_1$ and $R_2$ are the alkyl groups mentioned before.

The process of the invention produces lower acetals ($C_3$-$C_{24}$) having preferably from 3 to 12 carbon atoms, for example formaldehyde-dimethylacetal, -diethylacetal, -dipropylacetal, -dibutylacetal; acetaldehyde -dimethylacetal, -diethylacetal, -dipropylacetal, -dibutylacetal; propionaldehyde -dimethylacetal, -diethylacetal, -dipropylacetal, -dibutylacetal; butyraldehyde -dimethylacetal, -diethylacetal, -dipropylacetal and -dibutylacetal.

The acid solid catalysts are usually zeolites, alumina silicates, hydrotalcites or acidic ion exchange resins.

The adsorbent is usually an activated carbon, molecular sieves, zeolites, alumina silicates, alumina, silicates or acidic ion exchange resins.

The simulated moving bed reactor utilized in the present invention is a known apparatus and comprises 1 to 6 columns per zone; each column is packed with a solid or a mixture of solids. As depicted in FIG. 1 and FIG. 2, The SMB reactor typically has 4 or 5 zones. The reactor is equipped with a number of inlet and outlet ports, and a number of valves arranged in manner such that any feed stream may be introduced to any column and any outlet or effluent stream may be withdraw from any column. During the operation of the SMB unit, the columns to which the feed streams are fed and from which the outlet streams are withdrawn are periodically moved. To achieve separation of reaction products, the locations of the inlet and outlet streams are moved intermittently in the direction of the liquid flow. The intermittently port movement in the direction of the liquid flow simulates the counter-current of the bed or beds of the solid(s), e.g., the solid catalyst.

In the present invention two streams (desorbent and one feed) or three streams (desorbent and two feeds) could be introduced in the SMBR unit, where the desorbent is the same alcohol used to produce the acetal.

The first model of operation considers just one feed stream, as shown in FIG. 1. The feed is constituted by pure aldehyde, or a mixture of alcohol and aldehyde.

In the second operation model, the two reactants are introduced in two feed streams, accordingly to FIG. 2. Each feed stream could contain one of the pure reactants: one with the pure alcohol and the other with the pure aldehyde; or both feed streams are mixtures of alcohol and aldehyde, one richer in the alcohol and the other richer in the aldehyde.

Usually, the SMBR operates at the temperature from about 5° C. to 150° C. and at the pressure from about 100 kPa to 3500 kPa.

Preferably, the SMBR is kept at temperature from about 10° C. to about 70° C.

In the process of the present invention, the inlet/outlet streams are shifted periodically from the position P' to the position P, being that time named switching time.

The operation of the SMBR allows that the inlet/outlet streams shift, either forward or backward, in a synchronous or asynchronous way, within a switching period.

EXPERIMENTAL SECTION

The simulated moving bed reactor utilized in the present invention is a known apparatus (U.S. Pat. No. 2,985,589), comprising several columns connected in series; each column is packed with a solid or a mixture of solids. Two or three streams are introduced in the unit. One of them is the desorbent that is normally the alcohol used as reactant to form acetal; the desorbent is used to regenerate the solid in the first zone. The reactants (alcohol and aldehyde) could be introduced in a single feed stream (FIG. 1) or in two feed streams (FIG. 2). The products (acetal and water) are removed from the simulated moving bed reactor in two liquid streams; a first liquid stream comprising a solution of acetal in the desorbent (raffinate), and a second liquid stream comprising the water formed and the desorbent (extract). During the operation of the SMBR unit, the ports to which the feed streams are fed and from which the outlet streams are withdrawn are periodically shifted in the direction of the liquid flow. The intermittently port movement in the direction of the liquid flow simulates the counter-current between the solid(s) and the liquid. The reactor is equipped with a number of inlet and outlet ports, and a rotary valve or a number of valves arranged in manner such that any feed stream may be introduced to any column and any outlet or effluent stream may be withdraw from any column. The position of the inlet/outlet streams defines the different zones existing in the SMBR system, each one accomplishing a certain function and containing a variable number of columns.

In FIG. 1, the zone I is comprised between the desorbent stream port (D) and the extract stream port (X); the zone II is comprised between the extract stream port (X) and the feed stream port (F); the zone III is comprised between the feed stream port (F) and the raffinate stream port (R); and the zone IV is comprised between the raffinate stream port (R) and the recycle stream port (Rec). The reactants (alcohol and aldehyde) introduced in the feed stream (F) are converted within zones II and III. In these zones, the separation of the products formed (acetal and water) is carried out; the acetal is removed from the raffinate port and the water is removed from the extract port. As the products are removed from the reaction medium as they are formed, the equilibrium is shifted towards products formation. Therefore the aldehyde conversion increases to values above the thermodynamic equilibrium; being possible to achieve complete conversion (100%). The successful design of SMBR involves the right choice of the operation conditions, mainly the switching time period and flow rates in each section of the unit. The appropriate choice of those parameters will ensure the regeneration of acid solid (or mixture of solids) containing adsorbed water, in zone I; the regeneration of the desorbent contaminated with acetal in zone IV; and the complete conversion of reactants and the separation of the formed products in zones II and III. The flowrates for each section are given by the following expressions: $Q_I = Q_{Rec} + Q_D$; $Q_{II} = Q_I - Q_X$; $Q_{III} = Q_{II} + Q_F$; $Q_{IV} = Q_{III} - Q_R = Q_{Rec}$. The switching time, $t^*$, is the time necessary to shift all ports from the position P' to the position P. This process of shifting the ports could be realized synchronously or asynchronously.

The process of the present invention could be performed in a wide range of temperature and pressure. The temperature could vary from 5° C. up to 150° C.; preferably, from 10° C. up to 70° C.; and it is limited by the boiling points of the components at the pressure of operation of the SMBR. The pressure usually is not a critical issue, unless it is used to avoid vaporization of the components. Therefore, the pressure range is from atmospheric pressure until 3500 kPa.

The SMBR process schematically represented in FIG. 2 is similar to the one described before corresponding to FIG. 1. The main difference is that an additional feed stream is introduced to the system, leading to 5 zones of operation. This allows that the reactants are introduced separately in the system; one (the less adsorbed) carried out in stream $F_1$ and the other (the most adsorbed) in stream $F_2$. Alternatively, the feed $F_1$ can be a mixture of reactants richer in the less adsorbed one and the feed $F_2$ is a mixture richer in the most adsorbed reactant. The operation of this SMBR process is similar to the previous one: the regeneration of the acid solid and the desorbent is accomplished in zones I and V, respectively; and the complete conversion of reactants and separation of the formed products occurs in zones II, III and IV.

EXAMPLE

The process described in the present invention is better illustrated by the next example. The samples were analysed on a gas chromatograph and the compounds were separated in a fused silica capillary column, using a thermal conductivity detector for peak detection. The example concerns the synthesis of acetaldehyde diethylacetal from ethanol and acetaldehyde in a Simulated Moving Bed Reactor, using the acidic ion exchange resin Amberlyst 15 both as catalyst and as selective adsorbent. For this reaction, at room temperature and for a 2.2 initial molar ration of ethanol/acetaldehyde, the equilibrium conversion is of 55%.

The SMBR experiments were performed in a pilot unit LICOSEP 12-26 by Novasep (Vandoeuvre-dès- Nancy, France). Twelve columns Superformance SP 230×26 (length×i.d., m), by Götec Labortechnik (Mühltal, Germany), packed with the acid resin Amberlyst 15 (Rohm and Haas) were connected to the SMBR pilot unit. Each column is jacketed to ensure temperature control and the jackets are connected to one another by silicone hoses and to a thermostat bath (Lauda). Between every two columns there is a four-port valve actuated by the control system. When required, the valves allow either pumping of feed/eluent into the system or withdrawal of extract/raffinate streams. Each of the inlet (feed and eluent) and outlet (extract and raffinate) streams is pumped by means of HPLC pumps. The recycling pump is a positive displacement three-head membrane pump (Milton Roy, Pont St. Pierre, France), which may deliver flowrates as low as 20 ml/min up to 120 ml/min. The other flows (desorbent, extract, feed and raffinate) are controlled by four Merck—Hitachi pumps (Merck-Hitachi models L-6000 and L-6200, Darmstadt, Germany), connected to computer via RS-232. The maximum flow-rate in the desorbed and extract pumps is 30 ml/min, while in the feed and raffinate pumps is 10 ml/min. The maximum allowable pressure is 6 MPa. Between the twelfth and the first column there is a six-port valve, which is used to collect samples for internal concentration profile measurements. The equipment has its own process control software, which is able to accomplish the following tasks:

Switch the inlet and outlet streams at regular time intervals (as assigned by user) by opening and closing on-off pneumatic valves;

Keep steady and constant section flowrates as assigned;

Keep suction pressure at the recycling pump around a set point assigned by the user (usually 1500 kPa).

Each column was packed with Amberlyst 15, with an average particle diameter of 800 mm. The columns length, porosity and bulk density were of 23 cm, 0.4 and 390 kg/m$^3$, respectively. Tracer experiments were performed in all columns in order to determine the Peclet number (Pe), which allows the evaluation of the axial dispersion effects. The average value calculated to all twelve columns in the flowrates range used in the SMBR is Pe=300.

The feed was a mixture of ethanol (30%)/acetaldehyde (70%) and the desorbent was ethanol (99.5%). The flowrates were $Q_D$=50.0 ml/min; $Q_F$=10 ml/min; $Q_R$=25 ml/min; $Q_X$=35 ml/min and $Q_{Rec}$=20 ml/min. The switching time was set at 3.70 minutes and three columns per zone were used (FIG. 1). The internal concentration profiles at the middle of the switching time after the cyclic steady state be achieved are shown in FIG. 3. It is possible to observe that the acetaldehyde is practically completed converted, meaning that the conversion is near 100%. As it was mentioned before, the products are removed in different streams; the diethylacetal is carried out in the raffinate stream and the water in the extract. The product obtained in a fixed bed adsorptive reactor (FBAR) operating at steady state is compared with the raffinate product obtained in the SMBR, in terms of weight percentage, in the following table:

| Process | Ethanol | Acetaldehyde | Diethylacetal | Water |
| --- | --- | --- | --- | --- |
| FBAR | 31.89% | 12.50% | 48.25% | 7.36% |
| SMBR | 28.74% | 0.08% | 71.04% | 0.14% |

The acetaldehyde conversion at the outlet of the FBAR is 54.5%, near equilibrium value. For the SMBR the conversion is of 99.7%. Moreover, the raffinate product obtained in the SMBR contains 71% of diethylacetal with a weight purity of 99.7% without ethanol (98.4% molar); while the product of the FBAR contains 48% of diethylacetal with a weight purity of 70.8% without ethanol (37.1% molar).

REFERENCES

T. Aizawa, H. Nakamura, K. Wakabayashi, T. Kudo, H. Hasegawa, "Process for Producing Acetaldehyde Dimethylacetal", U.S. Pat. No. 5,362,918 (1994).

J. Andrade, D. Arntz, G. Prescher, "Method for Preparation of Acetals", U.S. Pat. No. 4,579,979 (1986).

L. W. Blair, S. T. Perri, B. K. Arumugam, B. D. Boyd, N. A. Collins, D. A. Larkin, C. W. Sink, "Preparation of Esters of Carboxylic Acids", U.S. Pat. No. 6,518,454 (2003).

L. W. Blair, E. B. Mackenzie, S. T. Perri, J. R. Zoeller, B. K. Arumugam, "Process for the Preparation of Ascorbic Acid", U.S. Pat. No. 6,476,239 (2002).

K. Boennhoff, "1,1-Diethoxyethane as Diesel Fuel", DE Patent No. 2 911 411 (1980).

K. Boennhoff, "Method for enhancing the ignition performance of dialkoxyalkanes used as diesel fuel, in particular 1,1-diethoxyethane", DE Patent No. 3 136 030 (1983).

V. Boesch, J. R. Herguijuela, "Process and Manufacturing Equipment for Preparing Acetals and Ketals", EP Patent No. 1 167 333 A2 (2001).

P. L. Bramwyche, M. Mudgan, H. M. Stanley, "Manufacture of Diethyl Acetal", U.S. Pat. No. 2,519,540 (1950).

A. Golubkov, "Motor Fuel for Diesel Engines", WO Patent No. 2001/0 181 154 A1 (2001).

A. Golubkov, I. Golubkov, "Motor Fuel for Diesel, Gas-Turbine and Turbojet Engines", US Patent No. 2002/0 026 744 A1 (2002).

M. M. Kaufhold, M. T. El-Chabawi, "Process for Preparing Acetaldehyde Diethyl Acetal", U.S. Pat. No. 5,527,969 (1996).

The invention claimed is:

1. A process for the preparation of acetals using a simulated moving bed reactor system to accomplish the conversion of reactants (aldehyde and alcohol) in the presence of an acid solid (or mixture of acid solids: catalysts and adsorbents) and, simultaneously, the separation of the reaction products (acetal and water) by selective adsorption.

2. Process according to claim 1, which comprises the following steps:
   I. to feed a reactant mixture (alcohol and aldehyde) and a desorbent (alcohol) to the SMBR unit, equipped with a series of columns packed with acid solid (or a mixture of acid solids);
   II. to react the alcohol with the aldehyde to produce acetal and water;
   III. to remove two streams, a first liquid stream comprising a solution of acetal in the desorbent (raffinate); a second liquid stream comprising the water formed and the desorbent (extract).

3. Process according to claim 1, wherein the simulated moving bed reactor comprises 4 or 5 zones, and each zones has several columns.

4. Process according to claim 1, the alcohol used as reactant has the following chemical structure

where $R_1$ represents an alkyl group $C_1$-$C_8$, lienar or branched.

5. Process according to claim 4, the referred alcohol can be methanol, ethanol, propanol and butanol.

6. Process according to claim 1, the aldehyde used as reactant has the following chemical structure

where $R_2$ represents an alkyl group $C_1$-$C_8$, linear or branched.

7. Process according to claim 6, the referred aldehyde can be formaldehyde, acetaldehyde, propionaldehyde and butyraldehyde.

8. Process according to claim 1, the acetal produced has the following chemical structure

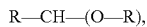

where $R_1$ and $R_2$ are the alkyl groups mentioned before.

9. Process according to claim 8, the referred acetal can be formaldehyde-dimethylacetal, -diethylacetal, -dipropylacetal, dibutylacetal; acetaldehyde-dimethylacetal, -diethylacetal, -dipropylacetal, -dibutylacetal; propi-onaldehyde-dimethylacetal, -diethylacetal, -dipropylacetal, -dibutylacetal; butyraldehyde-dimethylacetal, -diethylacetal, -dipropylacetal and -dibutylacetal.

10. Process according to claim 1, the acid solid catalyst is selected from zeolites, alumina silicates, hydrotalcites or acidic ion exchange resins.

11. Process according to claim 1, the adsorbent is selected from activated carbon, molecular sieves, zeolites, alumina silicates, alumina, silicates or acidic ion exchange resins.

12. Process according to claim 1, where two streams (desorbent and one feed) or three streams (desorbent and two feeds) could be introduced in the simulated moving bed reactor unit, where the desorbent is the same alcohol used to produce the acetal.

13. Process according to claim 12, wherein the feed is a stream of pure aldehyde, or a mixture of alcohol and aldehyde, when just one feed is introduced to the system.

14. Process according to claim 12, wherein the feeds are two separated streams of pure reactants (alcohol and aldehyde), or two mixtures of reactants, one richer in the alcohol and the other richer in the aldehyde, when two feeds are used.

15. Process according to claim 1, wherein the simulated moving bed reactor is operated at temperature from 5° C. to 150° C. and pressure from 100 kPa to 3500 kPa.

16. Process according to claim 15, wherein the simulated moving bed reactor is operated at temperature from 5° C. to 70° C.

17. Process according to claim 1, wherein the inlet/outlet streams are shifted periodically from the position P' to the position P, being that time named switching time.

18. Process according to claim 17, wherein the inlet/outlet streams are shifted, either forward or backward, in a synchronous or asynchronous way, within a switching period.

* * * * *